US012691189B2

(12) United States Patent
Rao

(10) Patent No.: US 12,691,189 B2
(45) Date of Patent: Jul. 28, 2026

(54) STERILIZATION OF AN OBJECT USING LOW ENERGY ELECTRON BEAM

(71) Applicant: PHARMALAB INDIA PVT. LTD., Maharashtra (IN)

(72) Inventor: M. Nageswara Rao, Gandhinagar (IN)

(73) Assignee: PHARMALAB IDIA PVT. LTD., Maharashtra (IN)

( * ) Notice: Subject to any disclaimer, the term of this patent is extended or adjusted under 35 U.S.C. 154(b) by 0 days.

(21) Appl. No.: 19/240,567

(22) Filed: Jun. 17, 2025

(65) Prior Publication Data

US 2025/0367334 A1     Dec. 4, 2025

Related U.S. Application Data

(63) Continuation of application No. 18/983,601, filed as application No. PCT/IN2022/051058 on Dec. 7, 2022.

(30) Foreign Application Priority Data

Jun. 23, 2022    (IN) .............................. 202221036188

(51) Int. Cl.
A61L 2/087 (2026.01)
H01J 29/04 (2006.01)
(Continued)

(52) U.S. Cl.
CPC .............. A61L 2/087 (2013.01); H01J 29/04 (2013.01); H01J 29/861 (2013.01); H01J 31/04 (2013.01);
(Continued)

(58) Field of Classification Search
CPC ................. A61L 2/087; A61L 2202/11; A61L 2202/121; A61L 2202/122; A61L 2202/14;
(Continued)

(56) References Cited

U.S. PATENT DOCUMENTS 7,767,987 B2 *  8/2010  Eguchi .................... A61L 2/087
                                                                    436/1
9,302,896 B2    4/2016  Drenguis et al.
(Continued)

FOREIGN PATENT DOCUMENTS

CN          101795716      5/2013
IN      1622KOLNP2003     11/2007

OTHER PUBLICATIONS

"Indian Application No. 202221036188, Examination Report dated Jan. 19, 2023", Jan. 19, 2023, 6 pgs.
(Continued)

*Primary Examiner* — Michael Maskell

(74) *Attorney, Agent, or Firm* — Schwegman Lundberg & Woessner, P.A.

(57) ABSTRACT

A sterilization device has been disclosed. The sterilization device comprises a toroidal housing having an outer wall, an inner wall, and a central cavity to receive an object to be sterilized. The toroidal housing comprises a thermionic cathode to release primary electrons, an anode grid to attract and accelerate the primary electrons to obtain accelerated primary electrons, and an anode wire to pull additional electrons released from a gas plasma discharge within the toroidal housing. The anode wire may accelerate the additional electrons and the accelerated primary electrons to create a spray of accelerated electrons that may be released through the inner wall. The spray of accelerated electrons may collide with the object to sterilize the object.

6 Claims, 6 Drawing Sheets

(51) Int. Cl.

| | |
|---|---|
| *H01J 29/86* | (2006.01) |
| *H01J 31/04* | (2006.01) |
| *H05H 1/24* | (2006.01) |

(52) U.S. Cl.
CPC ........ *H05H 1/4697* (2021.05); *A61L 2202/11* (2013.01); *A61L 2202/121* (2013.01); *A61L 2202/122* (2013.01); *A61L 2202/14* (2013.01); *A61L 2202/15* (2013.01)

(58) Field of Classification Search
CPC ..... A61L 2202/15; H01J 29/04; H01J 29/861; H01J 31/04; H05H 1/4697
USPC ................................................... 250/454.11
See application file for complete search history.

(56)                                References Cited

U.S. PATENT DOCUMENTS

| | | | | |
|---|---|---|---|---|
| 10,854,417 | B1 * | 12/2020 | Lewellen ................ | H01J 29/04 |
| 2016/0374261 | A1 * | 12/2016 | Rögner ................... | H01J 37/00 |
| | | | | 422/186.05 |
| 2019/0387605 | A1 * | 12/2019 | Weidauer ................ | G21K 5/02 |

OTHER PUBLICATIONS

"British Application No. 2500097.7, Examination Report dated Feb. 3, 2025", Feb. 3, 2025, 3 pgs.

\* cited by examiner

102

STERILIZATION OF AN OBJECT USING LOW ENERGY ELECTRON BEAM

CROSS-REFERENCE TO RELATED APPLICATIONS

This application is a continuation of U.S. application Ser. No. 18/983,601, filed 17 Dec. 2024, which is a U.S. National Stage Filing under 35 U.S.C. § 371 from International Application No. PCT/IN2022/051058 filed 7 Dec. 2022, which claims the benefit of priority to India Application No. 202221036188, filed 23 Jun. 2022, the benefit of priority of each of which is claimed herein, and which applications are hereby incorporated by reference herein in their entirety.

TECHNICAL FIELD

The subject matter described herein, in general, relates to a radiation-based system for continuous sterilization of an object in an open atmospheric condition, and more particularly, to a sterilization device and system for sterilizing an object by means of low energy electron beam streams having accelerated electrons.

BACKGROUND

The term "sterilization" generally refers to removal or inactivation of bio-contamination on a specific surface, from an object, or in fluid. Sterilization devices and methods are used in a broad range of applications and in multiple industries. For example, bottles may be sterilized before filling them with a liquid, medical equipments and/or devices may be sterilized before sale and before use, and food items, such as seeds, fruits, and vegetables, may be sterilized before further processing. Further, many industries may also perform sterilization of goods or products in bulk quantity. For example, sterilization may be done for a bulk of medical products, such as, containers storing a large number of test tubes.

BRIEF DESCRIPTION OF DRAWINGS

The detailed description is described with reference to the accompanying figures. It should be noted that the description and figures are merely examples of the present subject matter and are not meant to represent the subject matter itself.

Figure 1:
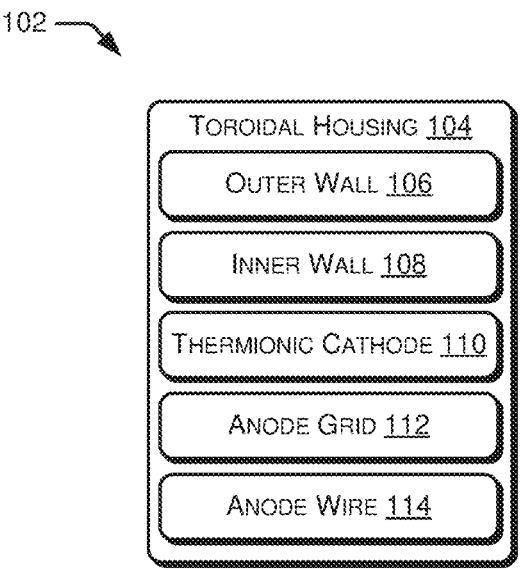
FIG. 1 illustrates a block diagram of a sterilization device, according to an example implementation of the present subject matter.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

With advancement in technology, different methods of performing sterilization have evolved. Example of such methods may include, but are not limited to, sterilization using steam, Ethylene oxide (EtO), X-ray, Gamma irradiation (γ-ray), and high energy electron beam. However, the conventional sterilization methods faced multiple challenges. For example, steam, may be used to sterilize an object in steam-based sterilization. Steam based sterilization may have advantage with limited industrial applications and may be effective method for sterilization of certain device types and objects which can tolerate high temperature and moisture. Steam based sterilization processes allow effective penetration of the steam sterilant because of latent heat transfer to all parts of a medical device and certain objects. Further, steam based sterilization is used for sterilizing heat stable liquids and particular polymers materials such as polypropylene, polycarbonates, polyurethanes, Tyvek, and other materials that are heat stable and can be sterilized using steam based sterilization method. However, steam based sterilization represents only a small percentage of the industry as materials used in food products, pharma packaging, and medical devices may be heat sensitive and not compatible with the high temperatures of the steam. High temperatures (typically 121-134° C.) can damage electronic devices, polymers, oxidize metals leading to corrosion, or cause combustion of lubricants in the devices. Further, the steam based sterilization may have limited application and may not be preferred to sterilize certain types of objects. In one example, steam-based sterilization may not be suitable for sterilizing electronic devices, for example, implants with electronic chips, and ophthalmic implants as the steam may damage the device or may lead to malfunctioning of the electronic device. Similarly, effectiveness of sterilization using ethylene oxide (EtO) may also be limited to surface of the object and mass sterilization may also not be feasible. Also, evacuation of EtO and its toxic degradation products, such as ethylene chlorohydrin and ethylene glycol, from the chamber is very critical and susceptible. Ethylene chlorohydrin and ethylene glycol are residual products formed during and after EtO sterilization. They result from decomposition of EtO in a sterilization chamber and on sterilization load over time. To remove the sterilant, a vacuum is created. Further, Nitrogen is used to "wash" the EtO from the devices to ensure the residual EtO gas concentration is below the flammable limit (approximately 3%). EtO emissions during medical device sterilization processes is a bigger concern due to several factors, for example, reactivity, flammability, toxicity, and emissions with materials limits its use for sterilization of liquids, pharmaceuticals, and biologics.

Further, sterilization methods based on high energy electron beam, X-ray, and Gamma irradiation (γ-ray) have high penetration and heavy barrier protection may thus be required to be installed to restrict emitted radiations in a confined area. Due to high radiation and penetration, such sterilization methods may not be performed in an open environment and without any heavy barrier protection. Also, multiple safety equipments may be required to be installed to handle any unwanted emergency or accidental situations, for example, leakage of radiations from a radioactive source being used. Further, such sterilization methods may require special materials that may not be easily available without special permission from a concerned authority. For example, Gamma ray (γ-ray) based sterilization methods may require radioactive compounds, such as Cobalt-60 (Co(60)), that may not be readily available without special permissions. Also, Cobalt-60 radio activity is reduced by ~1% per month. Therefore, consistency in dose rate is a concern and periodic calibration is needed. Also, a certain amount of isotope is annually required to compensate for decay. Getting new Cobalt-60 supply may be a prolonged and costly process. Thus, such sterilization methods may not be cost effective, easy to handle, readily scalable, and possess high risks.

The conventional sterilization methods may further include performing sterilization using low energy electron beam that are safer, have limited penetration, and negligible photons/X-rays emissions encourages safe operation. In such methods, an electron beam, or a spray of electron beams, having low energy may be emitted by a beam emitter. The emitted beams may bombard against an object to be sterilized. Bombardment of the electron beams on the object may break chains of Deoxyribonucleic acid (DNA) in living organisms, such as bacteria, resulting in microbial death and rendering the object sterile. To perform sterilization, the object may be passed through the beam emitter to sterilize the object from one side. The object may further be passed through another beam emitter that may be differently oriented, as compared to the previous beam emitter, to sterilize the object from another side. Similarly, the object may pass through multiple beam emitters that may be differently oriented to completely sterilize the object from all sides, externally and internally. In another implementation, multiple beam emitters, oriented at different angles, may be collectively arranged to sterilize the object from all sides. In yet another example, the object may be rotated after one side of the object is sterilized and the object may again be passed through the beam emitter to sterilize another side of the object. This process may be repeated until all sides of the object may be sterilized. Therefore, such sterilization methods are time consuming, require a lot of effort, and are not economical as multiple beam emitters are required to be installed and maintained. Further, arrangement and installation of multiple beam emitters may require a lot of space and load patterns shall be well defined each time to cover entire surfaces of an object being sterilized.

The present invention relates to a sterilization device to sterilize an object in open atmospheric conditions and in a continuous manner on a moving conveyor/mechanism. In one example of the present subject matter, the sterilization device maybe an irradiation sterilization device. The sterilization device may include a toroidal housing having an outer wall, an inner wall, and a central cavity formed by the inner wall to receive an object to be sterilized. In one example implementation, the toroidal housing may be an annulus housing in the shape of a circular ring having a circular void at the center of the circular ring, representing the central cavity of the toroidal housing. In another example implementation, the toroidal housing may be square or rectangular in shape and may have a square or a rectangular shaped void in the center of the toroidal housing.

In one example implementation, the toroidal housing may include a thermionic cathode, an anode grid, and an anode wire. In one example, the thermionic cathode may be a hot cathode that, when heated, may release electrons due to thermionic emission. The thermionic cathode may be electrically coupled with a low voltage supply unit to heat the thermionic cathode. The electrons within the thermionic cathode may receive sufficient energy to overcome forces keeping them within the thermionic cathode, thus leading to emission of electrons, hereinafter referred as primary electrons.

In one example implementation, the thermionic cathode may be coated with a work function emitter to emit further electrons, to increase the number of primary electrons. In one example, a work function may indicate a minimum energy required to remove an electron from Fermi level of a substrate to infinity. The work function emitter may thus be a material that may emit electrons on receiving the minimum energy, for example in the form of heat. The electrons emitted by the thermionic cathode and the work function emitter may collectively be referred to as the primary electrons. The primary electrons may be free electrons escaped from the thermionic cathode and the work function. These electrons may not be emitted with high velocity and may have low energy, and are thereby, referred to as low energy free electrons. These electrons may thus not form a beam and may need either electric or magnetic field to pull and accelerate the primary electrons to form an accelerated beam. The anode grid may attract the primary electrons from the thermionic cathode and accelerate the primary electrons to obtain accelerated primary electrons. For example, the anode grid may be supplied with a positive potential voltage from the low voltage supply unit, making the anode grid to be positively charged. The anode grid may thus attract the primary electrons towards the anode grid, therefore, accelerating the primary electrons.

Further, the toroidal housing may include a gas plasma discharge. In one example operation, a vacuum condition may be created inside the toroidal housing, as will be discussed below, before supplying any voltage to the thermionic cathode. Further, a gas may be injected into the toroidal housing from a gas supply unit connected with the toroidal housing. For example, the gas may be injected between the anode grid and the anode wire. A low voltage supply may then be provided to the anode grid and the anode wire. As would be known to a person skilled in the art, by passing an electric current through the gas, a fraction of constituents of the gas may be ionized due to break down into ion-electron pairs, forming a plasma. That is, after ionisation of gas atoms, a glow discharge called gas plasma, herein after referred as gas plasma discharge, may be formed. In other words, a volume of gas may contain a few randomly generated electrons. When a voltage is supplied across two electrodes (the anode wire and the anode grid) in the gas, these electrons are accelerated in the electric field between the electrodes. Various collisions among electrons, ions, and neutral gas molecules result in a breakdown. The plasma, or the gas plasma discharge, may thus be formed between the anode grid and the anode wire and may be a mixture of electrons, positive ions, and neutral gas molecules.

When the voltage is supplied to the thermionic cathode, the primary electrons may be accelerated, as discussed above. The accelerated primary electrons may collide with the electrons and ions of the gas plasma discharge to release further electrons and/or excite electrons present in the gas plasma discharge, hereinafter referred to as additional electrons. For example, when an accelerated primary electron collides with an ion, the accelerated electron may kick out an electron from the ion, leaving the ion in next highest charge state (charge increased by +1). Also, the accelerated electrons may collide with the electrons present in the gas plasma discharge to excite the electrons. Thus, due collision with the accelerated primary electrons, additional electrons may be released from the ions and electrons of the gas plasma discharge. The additional electrons and the primary electrons may again collide with remaining ions and electrons of the gas plasma discharge to release more additional electrons. The anode wire may pull the additional electrons released from the gas plasma discharge, thus accelerating the additional electrons. The anode wire may thus accelerate the additional electrons and the accelerated primary electrons to create a spray of accelerated electrons.

The spray of the accelerated electrons may then be released through the inner wall towards the object received by the central cavity. In one example, the inner wall comprises a perforated surface that may include one or more windows to release the spray of accelerated electrons towards the object received in the central cavity. The spray of accelerated electrons may thus bombard surfaces of the object, received in the central cavity, to remove or inactivate one or more pathogens that may be deposited on surfaces of the object. Since the object is placed in the central cavity and the toroidal housing surrounds the object, the spray of accelerated electrons may collide with all surfaces of the object. The object may thus be sterilized from all directions, or sides, using a single device, i.e., the toroidal housing. Therefore, there is no requirement to place multiple beam emitters, oriented in different directions, to sterilize the object from all sides.

Further, by using the thermionic cathode and the gas plasma discharge, the total number of accelerated electrons that may bombard the object may increase. Thus, the electrons released with low energy by the thermionic cathode may be released with high acceleration, leading to generation of a stronger, or higher energy, spray of electrons. Further, due to increased number of accelerated electrons bombarding the surface of the object, the spray of accelerated electrons may efficiently bombard with complete and all surfaces of the object. Also, the spray of the accelerated electrons may have sufficient energy, or acceleration, to sufficiently penetrate the object to sterilize the object from inside. For example, the object may be a package or a container that may include one or more articles to be sterilized. The object may be received in the central cavity and the spray of accelerated electrons may sterilize all surfaces of the object and also penetrate the object to sterilize the one or more articles stored inside the object. Therefore, mass sterilization of batches of objects and articles located inside the objects may be performed. The sterilization device may also be used, for example, for sterilizing liquids flowing through tubes or pipes, gases being transported through pipes, and objects of irregular shapes.

The present invention, thus, provides a solution to efficiently and completely sterilize an object from all sides without using multiple beam emitters. Further, the present invention provides a solution to the problems related with the conventional sterilization techniques that used steam, ethylene oxide (EtO), X-ray, Gamma irradiation (γ-ray), and high energy electron beam. For example, the sterilization device, as disclosed, may sterilize the object from all sides and with sufficient penetration to sterilize the object from inside without using any steam or chemicals. Also, unlike the Gamma irradiation (γ-ray) sterilization methods that use a radioactive source, the sterilization device may work on electricity that is much more safe, easily available, cheaper, and easy to handle. Further, the penetration is significantly less, but sufficient enough for sterilizing objects, as compared to high energy electron beams, X-rays, and Gamma ray (γ-ray) based sterilization methods. Since the penetration is less and there is no use of any radioactive source, there is no need to install any heavy protection barrier or shielding equipments for human beings. Further, the conventional sterilization methods required more time, for example hours to days, to sterilize a batch of objects, whereas the sterilization device may perform faster batch sterilization, for example in seconds or minutes. In general, most of the electron beams are very narrow (less than 10 mm) whereas the objects are larger and irregular shapes. The spray of accelerated electrons emitted by the sterilization device, disclosed herein, may provide avalanche of electron and scatter wider in air. This will reduce irradiation time and increase productivity, thereby sterilizing the objects in lesser time.

Further, the conventional Gamma irradiation (γ-ray) sterilization methods may not be environment friendly due to use of radioactive or nuclear elements. Whereas the sterilization device, disclosed herein, is environment friendly with no wastage, nuclear residue, or chemicals being involved in process of sterilization.

The present subject matter is further described with reference to FIGS. 1 to 4B. It should be noted that the description and figures merely illustrate principles of the present subject matter. Various arrangements may be devised that, although not explicitly described or shown herein, encompass the principles of the present subject matter. Moreover, all statements herein reciting principles, aspects, and examples of the present subject matter, as well as specific examples thereof, are intended to encompass equivalents thereof.

FIG. 1 illustrates a block diagram of a sterilization device 102, according to an example implementation of the present subject matter. In one example implementation, the sterilization device 102 may include a toroidal housing 104 having an outer wall 106, an inner wall 108, and a central cavity (not shown in this figure) formed by the inner wall 108 to receive an object to be sterilized. The toroidal housing 104 may further include a thermionic cathode 110, an anode grid 112, and an anode wire 114.

In one example implementation, a vacuum may be created inside the toroidal housing 104 and a gas may be injected. For example, the gas may be injected between the anode grid 112 and the anode wire 114. A low voltage supply may then be provided to the anode grid and the anode wire. For example, the gas may be injected between the anode grid and the anode wire. A low voltage supply may then be provided to the anode grid and the anode wire. By passing an electric current through the gas, constituents of the gas may be ionized due to break down into ion-electron pairs, forming a plasma. That is, after ionisation of gas atoms, a glow discharge called gas plasma, herein after referred as gas plasma discharge, may be formed.

Further, the thermionic cathode 110 may be electrically coupled with a low voltage supply unit (not shown in this figure) and may be supplied a negative potential voltage. The low voltage supply may heat the thermionic cathode 110 and electrons within the thermionic cathode may receive sufficient energy to overcome forces keeping them within the thermionic cathode 110, thus leading to emission of one or more primary electrons. The anode grid 112 may subsequently attract the one or more primary electrons, thus accelerating the primary electrons to obtain accelerated primary electrons. In one example, the anode grid 112 may be electrically coupled with the low voltage supply unit and may be supplied with a positive potential voltage. The positive potential voltage may positively charge the anode grid 112. The anode grid 112 may thus attract and accelerate the one or more primary electrons emitted from the thermionic cathode 110 to obtain accelerated primary electrons.

Further, the accelerated primary electrons may collide with the ions and/or electrons of the gas plasma discharge. The collision may release one or more additional electrons, herein after interchangeably referred to as additional electrons. For example, when an accelerated primary electron collides with an ion of the gas plasma discharge, the accelerated electron may kick out an electron from the ion, leaving the ion in next highest charge state (charge increased by +1). Also, when the accelerated primary electrons collide with electrons of the gas plasma discharge, the electrons of the gas plasma discharge may get into an excited state. Thus, on collision with the accelerated primary electrons, the ions and the electrons of the gas plasma discharge may release the additional electrons.

In one example implementation, the anode wire 114 may pull the additional electrons released from the gas plasma discharge. In one example, the anode wire 114 may be electrically coupled with a voltage supply unit (not shown in this figure) and may be supplied with a positive potential voltage. The anode wire 114 may thus be positively charged and may pull the additional electrons and the accelerated primary electrons towards the anode wire 114, creating a spray of accelerated electrons. The spray of the accelerated electrons may then be released through the inner wall 108 towards the object received by the central cavity. In one example, the inner wall 108 may include a perforated surface to release the spray of accelerated electrons towards the object received in the central cavity. The spray of accelerated electrons may thus bombard at least one surface of the object to sterilize the object by inactivating one or more microorganisms that may be deposited on the surface of the object.

Figure 2:
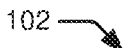
FIG. 2 illustrates a block diagram of the sterilization device, according to another example implementation of the present subject matter.
Figure 2:
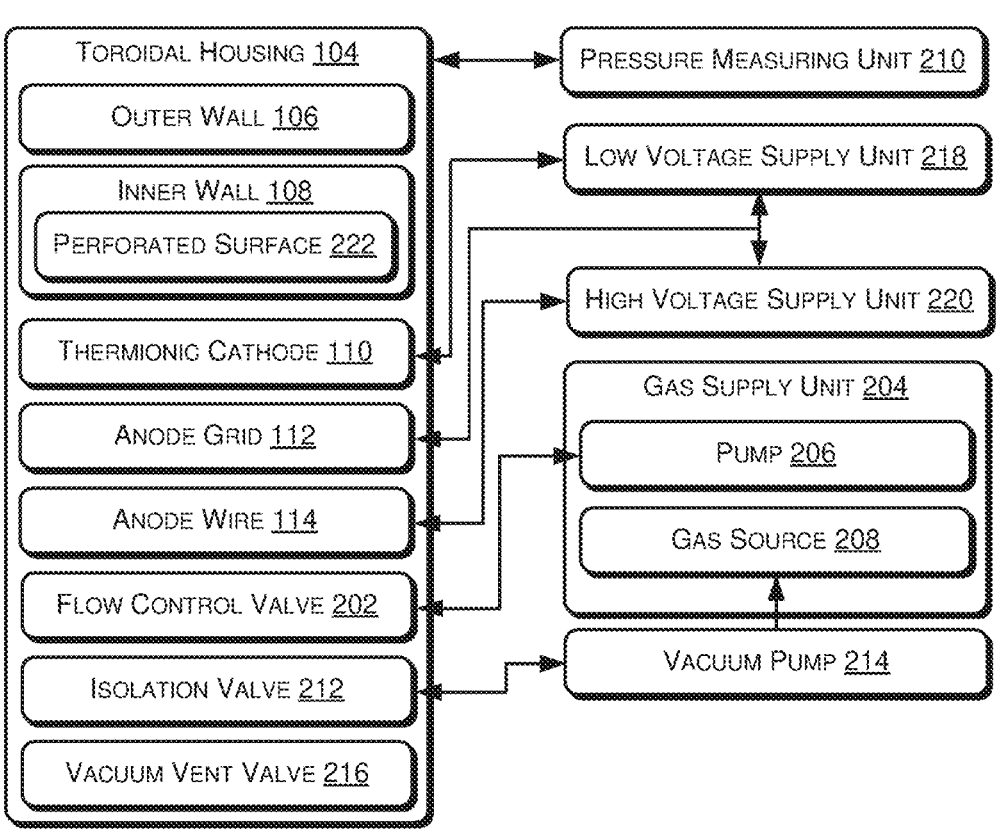

FIG. 2 illustrates a block diagram of the sterilization device 102, according to another example implementation of the present subject matter. In one example, the sterilization device 102 may be used to sterilize one or more objects. Examples of the objects may include, but are not limited to, bottles, seeds, fruits, vegetables, medical implants, electronic devices, medical equipments, fabrics, surgical instruments, adhesives, plastics, cellulosics, glass and ceramics, labware, single use medical, and pharmaceutical packaging, and other temperature sensitive sterile products. The sterilization device 102 may also be used, for example, for sterilizing packages storing one or more objects, liquids flowing through tubes or pipes or stored in a bottle or a container, gases being transported through pipes, and other objects of irregular shapes and sizes.

In one example implementation, the sterilization device 102 may include the toroidal housing 104 formed by the outer wall 106 and the inner wall 108. In one example, the outer wall 106 and the inner wall 108 may be positioned such that a hollow space is formed between the outer wall 106 and the inner wall 108 making the toroidal housing 104 hollow from inside. Further, the inner wall 108 may be joined end-to-end to form a central cavity of the toroidal housing 104. The toroidal housing 104 may be of any shape. In one example, the toroidal housing 104 may be a 3-dimensional parallelogram with a parallelogram shaped void in center of the toroidal housing 104, representing the central cavity of the toroidal housing 104. In another example, the toroidal housing 104 may be an annulus housing in a 3-dimensional circular ring with a circular void at center of the circular ring, representing the central cavity of the toroidal housing 104. The toroidal housing 104 may be made of any material. In one example, the toroidal housing 104 may be made of an electrically insulating material. In another example, the toroidal housing 104 may be made from a metal or a combination of metals. For example, the toroidal housing 104 may be made from any one of carbon steel, stainless steel, aluminum, or a combination thereof.

Further, the toroidal housing 104 may be filled with a gas, as discussed in FIG. 1. Examples of the gas may include, but are not limited to, Nitrogen, Argon, Helium, Pure air, Hydrogen, and Carbon dioxide. In one example, the toroidal housing 104 may include a flow control valve 202 that may be in fluid communication with a gas supply unit 204 to receive the gas. The flow control valve 202 may control injection of the gas from the toroidal housing 104. In a closed state, the flow control valve 202 may restrict passage of the gas, from the gas supply unit 204, into the toroidal housing 104. Whereas, in an open state, the flow control valve 202 may allow passage of the gas from the gas supply unit 204 into the toroidal housing 104. The gas may then be injected in the toroidal housing 104. In one example, the gas supply unit 204 may include a pump 206 that may be in fluid communication with a gas source 208. The gas source 208 may be a source capable of supplying the gas. For example, the gas source 208 may be a pressurized cylinder filled with the gas or a pipeline connected with a source capable of supplying the gas. The pump 206 may supply the gas, from the gas source 208, with a predefined pressure. The toroidal housing 104 may further be connected with a pressure measuring unit 210 to measure a pressure of the gas inside the toroidal housing 104. In one example, the pressure measuring unit 210 may include a Pirani Gauge.

Further, in one example, the toroidal housing 104 may be in fluid communication with an isolation valve 212. The isolation valve 212 may be in fluid communication with a vacuum pump 214 to create a vacuum inside the toroidal housing 104. In a closed state, the isolation valve 212 may keep the toroidal housing 104 leak tight by preventing any leakage of the gas during operation. An outlet of the isolation valve 212 may be connected to the vacuum pump 214 and may isolate vacuum pump suction during electron beam generation inside the toroidal housing 104. Whereas, in an open state, the isolation valve 212 may allow evacuation of the gas filled inside the toroidal housing 104 to achieve a desired vacuum level to generate gas plasma discharge. In one example, when the isolation valve 212 is in the open state and the vacuum pump 214 is being operated, the gas filled inside the toroidal housing 104 may be drawn out, thus creating the vacuum inside the toroidal housing 104. In one example, the isolation valve 212 may also act as a safety valve that may release the gas filled inside the toroidal housing 104 to maintain a required pressure inside the toroidal housing 104. When a pressure of the gas increases above a predefined pressure level, the isolation valve 212 may open to release the gas in order to avoid occurrence of any unwanted situation, for example, explosion of the toroidal housing 104 due to high pressure built inside the toroidal housing 104.

In one example, the toroidal housing 104 may further include a vacuum vent valve 216 to break a vacuum and bring normal atmospheric condition inside the toroidal housing 104. For example, in an open state, the vacuum vent valve 216 may suck free air from the atmosphere to break the vacuum inside the toroidal housing 104. In the closed state, the vacuum vent valve 216 may act as a seal that may prevent any leakage of the gas filled inside the toroidal housing 104. Examples of the flow control valve 202, the isolation valve 212, and the vacuum pump 214 may include, but are not limited to, a ball valve, a butterfly valve, a globe valve, a gate valve, a plug valve, a diaphragm valve, a bellows angle valve, a reducing valve, and a needle valve. The flow control valve 202, the isolation valve 212, and the vacuum vent valve 216 may operate electrically, pneumatically, or Electro-pneumatically.

In one example, the toroidal housing 104 may include the thermionic cathode 110, the anode grid 112, and the anode wire 114. In one example, the thermionic cathode 110, the anode grid 112, and the anode wire 114 may be placed within the hollow space formed inside the toroidal housing 104. In one example implementation, the thermionic cathode 110 may be placed in close proximity with the outer wall 106, the anode grid 112 may be placed in close proximity to the thermionic cathode 110, and the anode wire 114 may be placed adjacent to the anode grid 112 and in close proximity with the inner wall 108, as illustrated in FIG. 3B.

In one example implementation, before operation or when operation of the toroidal housing 104 is to be initiated, a vacuum condition may initially be created inside the toroidal housing 104. For example, the flow control valve 202 may be operated in the open state and the vacuum pump 214 may be initiated to evacuate the toroidal housing 104. Further, the gas may be injected into the toroidal housing 104 from the gas supply unit 204 via the flow control valve 202. For example, the gas may be injected between the anode grid 112 and the anode wire 114. A low voltage supply may then be provided to the anode grid 112 and the anode wire 114. In one example, the anode grid 112 and the anode wire 114 may be electrically coupled with a low voltage supply unit 218 to receive electric current. Examples of the low voltage supply unit 218 may include, but are not limited to, an Alternating Current (AC) power source and a Direct Current (DC) power source.

As would be understood, by passing an electric current through the gas, a fraction of constituents of the gas may be ionized due to break down into ion-electron pairs, forming a conductive plasma. That is, after ionisation of gas atoms, a glow discharge called gas plasma, being referred as the gas plasma discharge, may be formed. In other words, a volume of gas may contain randomly generated electrons. When a voltage is supplied across the two electrodes (the anode wire 114 and the anode grid 112) in the gas, these electrons are accelerated in the electric field between the electrodes. Various collisions among electrons, ions, and neutral gas molecules result in a breakdown. The plasma, or the gas plasma discharge, may thus be formed between the anode grid 112 and the anode wire 1 and may be a mixture of electrons, positive ions, and neutral gas molecules.

After the gas plasma discharge, the thermionic cathode 110 may be operated to initiate release of the one or more primary electrons. In one example implementation, electric current may be supplied to the thermionic cathode 110 to initiate release of the one or more primary electrons. In one example, the thermionic cathode 110 may be a hot cathode electrode that may emit primary electrons due to thermionic emission. The thermionic cathode 110 may include a filament made from a refractory metal, for example, tungsten. The thermionic cathode 110 may be electrically coupled with the low voltage supply unit 218 to receive electric current to heat the filament. For example, the thermionic cathode 110 may be electrically coupled with a negative terminal of the low voltage supply unit 218, as illustrated in FIG. 3B, to receive a negative potential voltage to heat the thermionic cathode 110. In one example, the thermionic cathode 110 may be provided a negative potential voltage in a range of −100 to −500 V and current in a range of 1 to 2

Ampere. By heating of the filament, electrons within the thermionic cathode 110 may receive energy to overcome forces keeping them within the thermionic cathode 110, thus leading to emission of the primary electrons.

In one example, the thermionic cathode 110 may be a cathode electrode in the shape of a flat plate. In another example, the thermionic cathode 110 may be a conical shaped cathode electrode, as illustrated in FIG. 3B. In yet another example, the thermionic cathode 110 may be a parabolic shaped cathode electrode. Having the conical or parabolic shaped cathode electrode may increase charge concentration at nose of the surface area available for electron emission as compared to electrodes in form of a flat plates or other planar geometries. Due to the converging surface area, significantly more primary electrons may be emitted from the surface of the thermionic cathode 110. Also, due to the conical or parabolic shape, the strong electric field at the nose end can knock off ample of primary electrons that may interact with the gas plasma discharge. As a result, production of secondary electrons may increase inside the toroidal housing 104 and may spread over more area, instead of forming a focused narrow beam of primary electrons.

In one example implementation, the thermionic cathode 110 may be coated with the work function emitter (not shown) to increase the number of primary electrons emitted from the thermionic cathode 110. In one example, a work function may indicate a minimum energy required to withdraw an electron from Fermi level of a substrate to infinity. The work function emitter may thus be a material that may emit electrons on receiving the minimum energy, for example in the form of heat. The work function emitter may thus be coated on the thermionic cathode 110 and may emit additional electrons due to heating of the thermionic cathode 110. The electrons emitted by the thermionic cathode 110 and the work function emitter may be hereinafter collectively referred to as the primary electrons. Examples of the work function emitter may include, but are not limited to, at least one of a Lanthanum hexaboride (LaB6), Barium hexaboride (BaB6), Barium oxide (BaO/BaO2) zirconium diboride (ZrB2), hafnium nitride (HfN), and a Cerium hexaboride (CeB6).

In one example implementation, the primary electrons released by the thermionic cathode 110 may be attracted towards the anode grid 112, placed in close proximity to the thermionic cathode 110. The anode grid 112 may attract and accelerate the one or more primary electrons to obtain accelerated primary electrons. In one example, the anode grid 112 may be an anode electrode in the form of a grid or a mesh that may be electrically coupled with a positive terminal of the low voltage supply unit 218, as illustrated in FIG. 3B. The anode grid 112 may be made of, for example, titanium, stainless steel, and nickel. The low voltage supply unit 218 may supply a positive potential voltage to the anode grid 112. Due to the positive potential voltage, the anode grid 112 may be positively charged and attract the primary electrons, thereby accelerating the primary electrons.

The accelerated primary electrons may collide with the ions and/or electrons of the gas plasma discharge filled in the toroidal housing 104, as discussed above. In one example, the primary electrons may collide with the ions and/or electrons of the gas plasma discharge to release the one or more additional electrons from the gas plasma discharge. The additional electrons and the primary electrons may further collide with the ions and the electrons, remaining in the gas plasma discharge after collision, to further release additional electrons. Similarly, the additional electrons and the primary electrons may collide multiple times with remaining ions and/or the electrons of the gas plasma discharge to release further additional electrons.

In one example, the anode wire 114 may pull the one or more additional electrons emitted from collisions of the additional electrons and the primary electrons with the ions and/or electrons of the gas plasma discharge. In one example, the anode wire 114 may be in form of a cylindrical electrode that may be electrically coupled with a high voltage supply unit 220. A positive terminal of the high voltage supply unit 220 may be electrically coupled with the anode wire 114 to supply a positive potential voltage and floating power supply with the anode grid 112 and low voltage power supply output end, as illustrated in FIG. 3B. In one example, the high voltage supply unit 220 may supply a voltage in a range of 150-300 kV. The anode wire 114 may thus carry positive charge and, therefore, pull the additional electrons. Pulling the additional electrons may accelerate the additional electrons. Further, due to the positive charge, the anode wire 114 may attract the accelerated primary electrons, thereby, further accelerating the accelerated primary electrons. Therefore, the anode wire 114 may create a spray of accelerated electrons, comprising the accelerated additional electrons and the further accelerated primary electrons.

The spray of accelerated electrons may be released through the inner wall 108 towards the object received by the central cavity. In one example, the inner wall 108 may include a perforated surface 222 to release the spray of accelerated electrons towards the object. The perforated surface 222 may include one or more windows to release the spray of accelerated electrons. In one example, the perforated surface 222 may be made from stainless steel and the inner wall 108 may be made from a Tungsten window foil of 15-20 micron thickness. The one or more windows may allow the spray of the accelerated electrons to exit the inner wall 108.

The spray of accelerated electrons may thus collide with at least one surface of the object to sterilize the object. In one example, since the object is placed inside the central cavity all the sides of the object may receive, or be bombarded with the spray of accelerated electrons, as illustrated in FIG. 3C. Therefore, all sides of the object may be sterilized.

Figure 3A:
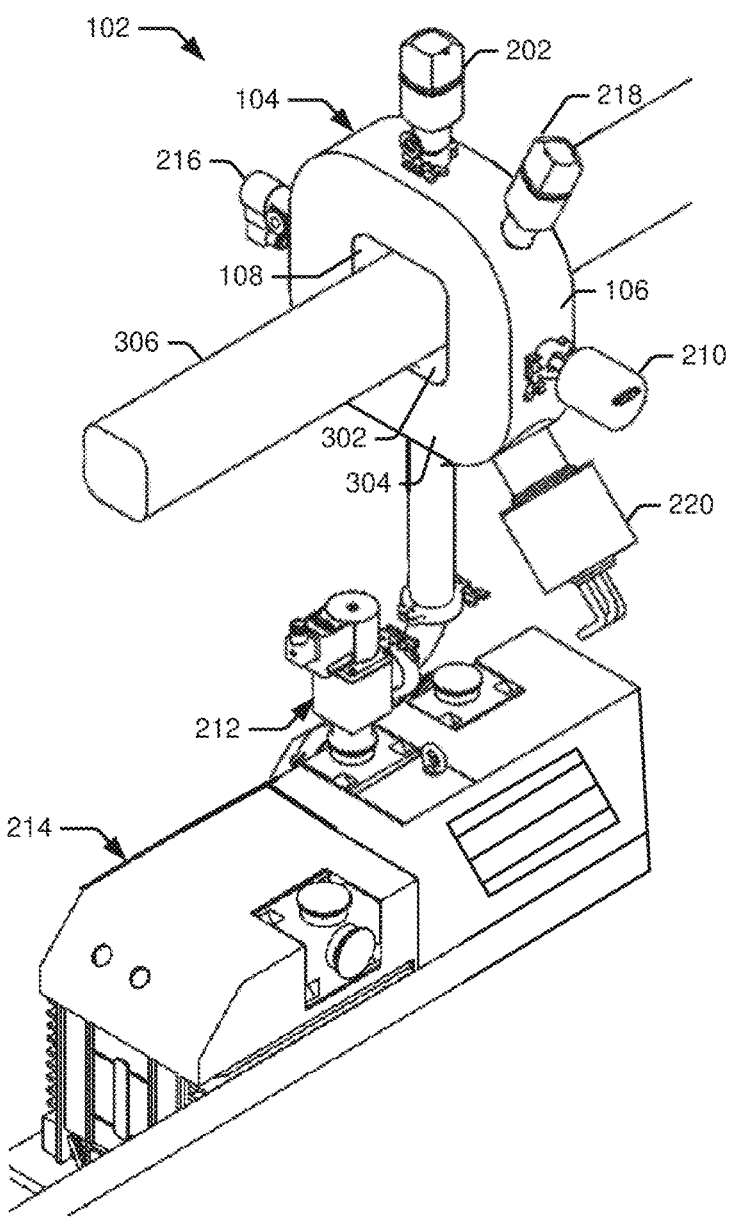
FIG. 3A illustrates the sterilization device, according to an example implementation of the present subject matter.
Figure 3B:
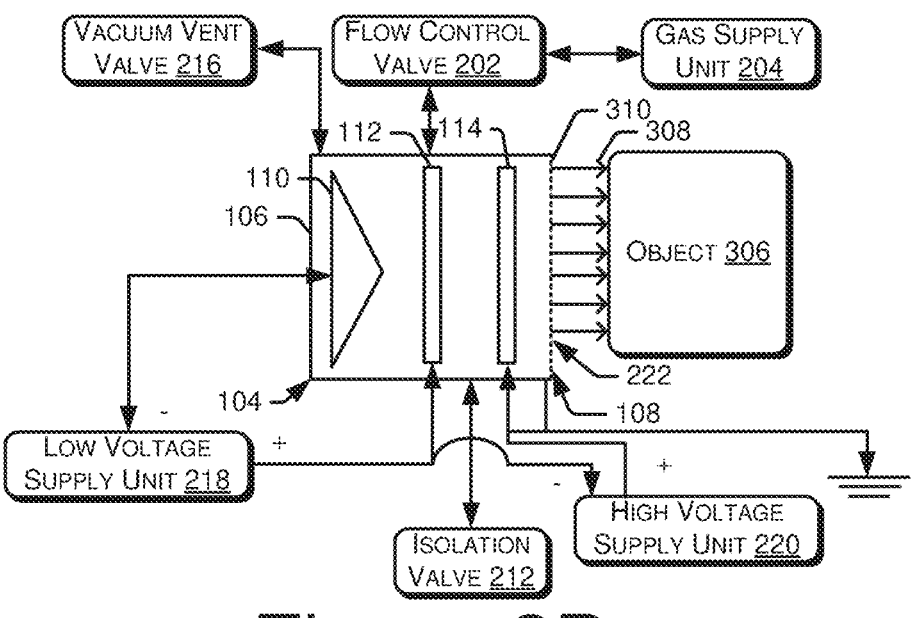
FIG. 3B illustrates a cross-sectional view of a toroidal housing, according to an example implementation of the present subject matter.
Figure 3C:
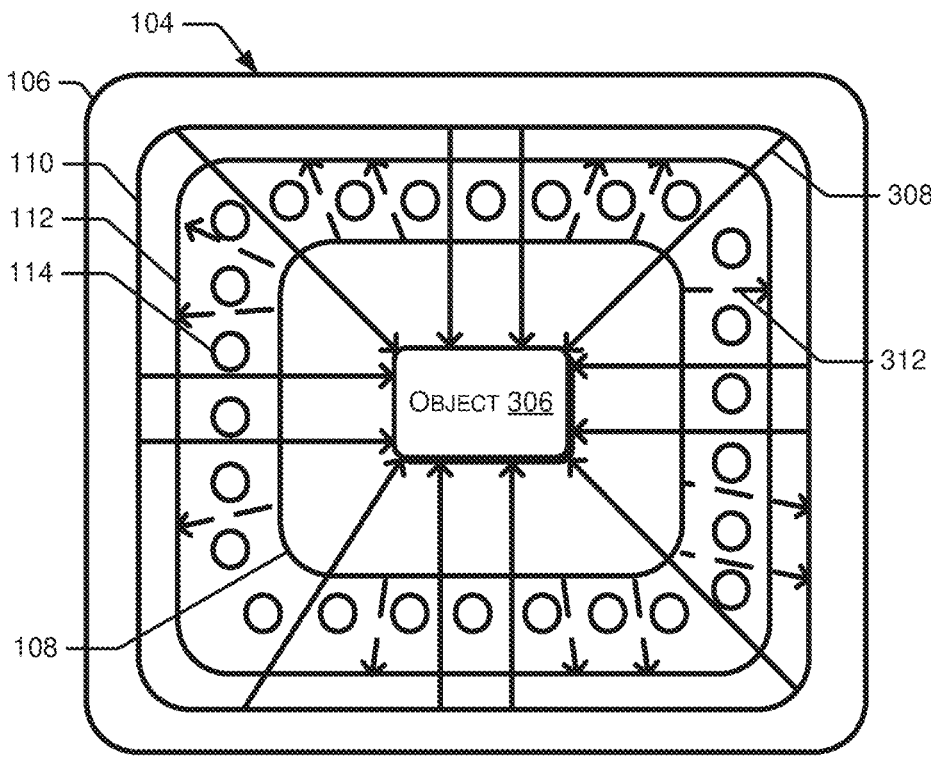
FIG. 3C illustrates emission of a spray of electrons on an object, according to an example implementation of the present subject matter.

FIG. 3A illustrates the sterilization device 102, according to an example implementation of the present subject matter. FIG. 3B illustrates a cross-sectional view of the toroidal housing 104, according to an example implementation of the present subject matter. FIG. 3C illustrates emission of the spray of electrons on an object, according to an example implementation of the present subject matter. As discussed above, the sterilization device 102 may include the toroidal housing 104 formed by the outer wall 106, the inner wall 108, and a central cavity 302, such as the central cavity discussed in FIGS. 1 and 2. The toroidal housing 104 may further include a front wall 304 and a rear wall (not shown) to enclose the hollow space formed between the outer wall 106 and the inner wall 108. As previously described, the toroidal housing 104 may be of any shape. In one example, the toroidal housing 104 may be a substantially square shaped annulus housing with a substantially square shaped central cavity 302, as illustrated. The central cavity 302 may receive an object 306 for sterilization. As discussed above, the toroidal housing 104 may further include the thermionic cathode 110 placed in close proximity with the outer wall 106, the anode grid 112 placed in close proximity to the thermionic cathode 110, and the anode wire 114 placed adjacent to the anode grid 112 and in close proximity with the inner wall 108.

In one example implementation, the vacuum pump 214 may then be operated to create vacuum inside the toroidal housing 104. After creating the vacuum, the toroidal housing 104 may be filled with the gas for gas plasma discharge by the gas supply unit 204. In one example, the toroidal housing 104 may further be connected with the pressure measuring unit 210 to measure a pressure of the gas filled inside the toroidal housing 104. When the pressure of the gas increases above a predefined pressure level inside the toroidal housing 104, the isolation valve 212 may release the gas filled inside the toroidal housing 104.

Once the toroidal housing 104 is filled with the gas, the low voltage supply unit 218 and the high voltage supply unit 220 may be operated. In one example, the low voltage supply unit may be electrically coupled with the thermionic cathode 110 and the anode grid 112, as well as the floating power supply of the high voltage supply unit 220 output end, as illustrated in FIG. 3B. Further, the thermionic cathode 110 may be the hot cathode electrode that may release the primary electrons due to thermionic emission, as discussed above. In one example, the thermionic cathode 110 may be electrically coupled with a negative terminal of the low voltage supply unit 218 and may be provided a negative potential voltage of −150 keV (kilo electron Volt) to heat the thermionic cathode 110. Due to heat, electrons within the thermionic cathode 110 may receive energy to overcome forces keeping them within the thermionic cathode 110, thus causing the thermionic cathode 110 to emit the primary electrons. In one example implementation, the thermionic cathode 110 may be coated with the work function emitter (not shown) to increase the number of electrons in the primary electrons emitted from the thermionic cathode 110, as discussed above.

The primary electrons released by the thermionic cathode 110 may be attracted towards the anode grid 112. In one example, the anode grid 112 may be electrically coupled with the positive terminal of the low voltage supply unit 218 and be provided with a positive potential voltage. Due to the positive potential voltage, the anode grid 112 may be positively charged and may thus attract the primary electrons, thereby accelerating the primary electrons. The accelerated primary electrons may collide with the ions and/or electrons of the gas plasma discharge present in the toroidal housing 104, as discussed above. In one example, the primary electrons may collide with the ions and/or electrons of the gas plasma discharge to release the additional electrons. The additional electrons and the primary electrons may further collide with the ions and/or electrons, remining in the gas plasma discharge after collision, to further release additional electrons. Similarly, a chain of collisions between the additional electrons, the primary electrons, and remaining ions and/or electrons of the gas plasma discharge may occur to release the additional electrons.

Further, the anode wire 114 may pull the additional electrons. In one example, the anode wire 114, being electrically coupled with the positive terminal of the high voltage supply unit 220, may receive a positive potential voltage, for example, a voltage of 150 kV (kilo Volt). The anode wire 114 may thus carry positive charge and, therefore, attract the additional electrons towards the anode wire 114. The additional electrons may thus be accelerated. Also, due to the positive charge, the anode wire 114 may attract the accelerated primary electrons, thereby, further accelerating the already accelerated primary electrons. Therefore, the anode wire 114 may create the spray of accelerated electrons, as illustrated by arrows 308, in the FIG. 3C, comprising the accelerated additional electrons and the further accelerated primary electrons.

The spray of accelerated electrons may then be released through the inner wall 108 towards the object 306 received by the central cavity 302. In one example, the inner wall 108 may include the perforated surface 222 having one or more windows 310 (illustrated with dashed lines, where opening between the dashes may represent the windows 310) to release the spray of accelerated electrons. In one example, the perforated surface 222 may be made from a temperature resistive high strength metal foil. The spray of accelerated electrons may thus collide with at least one surface of the object 306 to sterilize the object 306. In one example, since the object 306 is placed inside the central cavity 302 that may be surrounded by the inner wall 108, as illustrated in FIG. 3A, all the sides of the object 306 may receive, or be bombarded, with the spray of accelerated electrons, as illustrated in FIG. 3C.

FIG. 3C illustrates emission of the spray of electrons on the object 306, according to an example implementation of the present subject matter. As discussed above, the spray of accelerated electrons, represented by arrows 308, may be released through the inner wall 108 towards the object 306 received by the central cavity 302. As the object 306 is placed inside the central cavity 302, or may pass through the central cavity 302, the inner wall 108 may surround the object 306. The spray of electrons released from the inner wall 108 may thus collide with all the sides of the object 306, thereby completely sterilizing the object 306 from all sides.

Further, the ions of the gas plasma may release electrons due to collisions with the additional electrons and the accelerated primary electrons, as discussed above. Emission of electrons from the ions may leave the ions in next highest charge state. For example, release on an electron from an ion may increase the charge of the ion by +1. Similarly, when multiple ions release multiple additional electrons, respectively, the charge of the ions may increase, thus making the ions positively charged. In one example implementation, since the thermionic cathode 110 is supplied with the negative potential voltage, the thermionic cathode 110 may tend to be negatively charged. The thermionic cathode 110 may thus attract the positively charged ions (movement of the positively charged ions is illustrated with dashed line arrows 312).

Once the object 306 is sterilized, the flow control valve 202 may be operated to be in the open state to allow release of the gas plasma discharge filled the toroidal housing 104 and create the vacuum inside the toroidal housing 104.

Figure 4A:
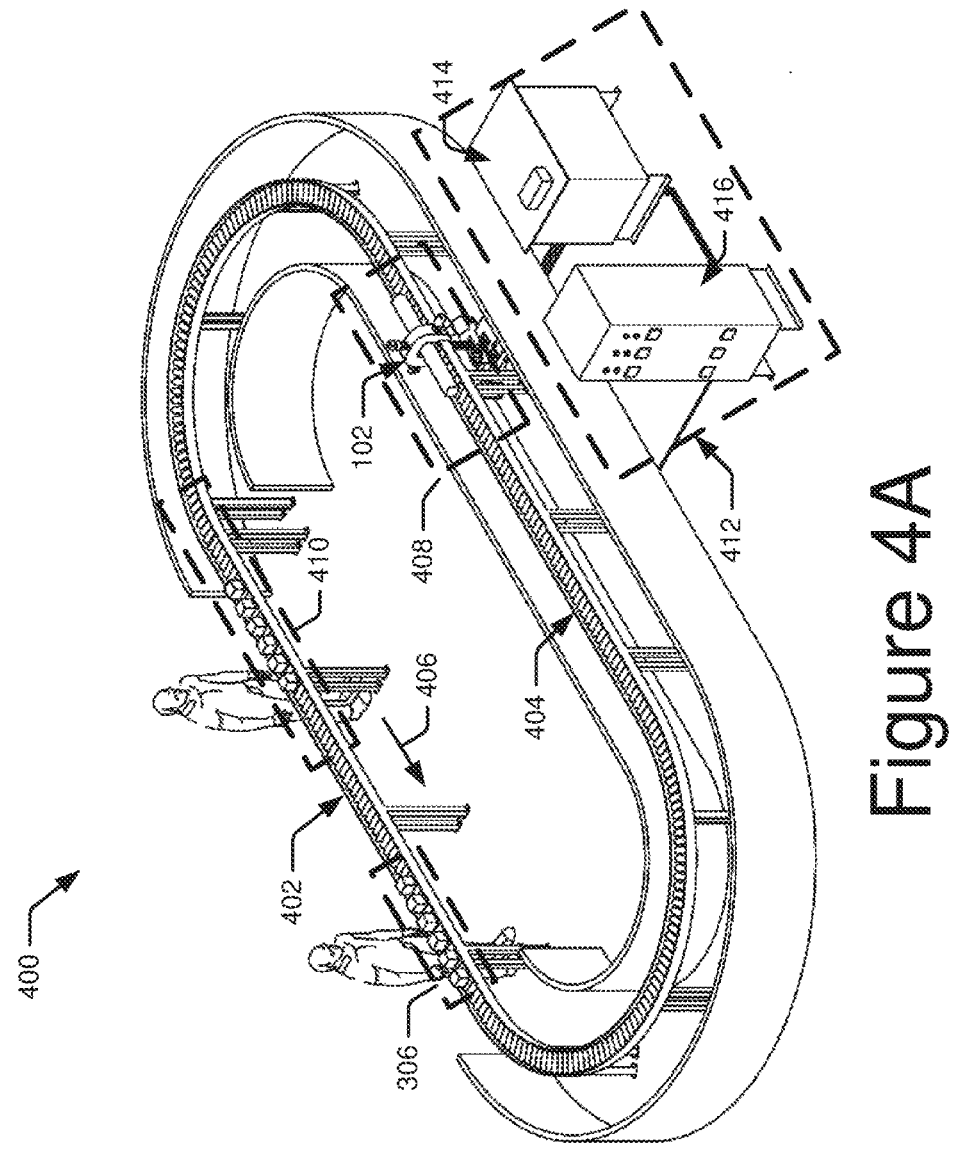
FIGS. 4A and 4B illustrate a system for sterilizing an object, according to an example implementation of the present subject matter.
Figure 4B:
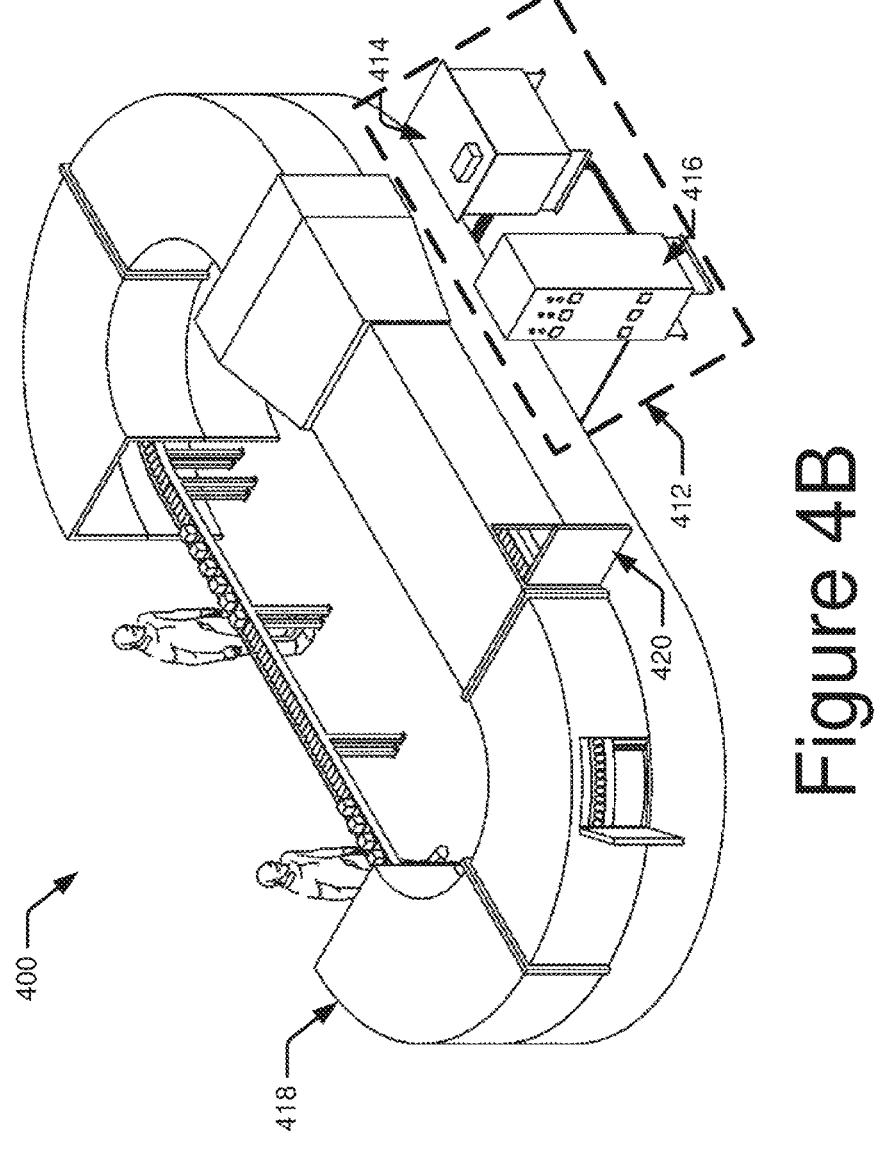

FIGS. 4A and 4B illustrate a system 400 for sterilizing an object, according to an example implementation of the present subject matter. The system 400 may be installed in any industry, for example, in food packaging or food processing industry, medical equipments or medical devices manufacturing industry, beverage industry, textile industry, pharmaceutical industry, and the like to perform sterilization. The system 400 may include a conveyor unit 402 to receive the object, such as the object 306, and a sterilization device, such as the sterilization device 102 discussed in FIGS. 1 to 3C, for sterilizing the object 306. As illustrated, the conveyor unit 402 may also receive multiple objects 306 for sterilization. The multiple objects 306 may interchangeably and collectively be referred as the object 306 or objects 306.

In one example implementation, the conveyor unit 402 may include a movable conveyor 404 to receive the object 306 to be sterilized. In one example, the movable conveyor 404 may include a conveyor belt that may move in a direction illustrated by an arrow 406. In another example, the movable conveyor 404 may include multiple rollers that may rotate towards a direction illustrated by an arrow 406. In one example, the conveyor unit 402 may include one or more motors (not shown) to move the movable conveyor 404 in the direction illustrated by the arrow 406. In one example, a worker located near the movable conveyor 404 may load the object 306 to be sterilized on the movable conveyor 404. In another example, one or more robots, for example robotic arms, may be located near the movable conveyor 404 to load the object 306 on the movable conveyor 404.

Further, the movable conveyor 404 may move towards a sterilization section 408 of the conveyor unit 402 to sterilize the object 306. In one example, the sterilization section 408 may include the sterilization device 102. In one example implementation, the sterilization device 102 may include the toroidal housing 104 that may sterilize the object 306, as discussed in FIGS. 1 to 3C. The sterilized object 306 may then move to a finalization section 410 of the conveyor unit 402. In one example, the movable conveyor 404 may move towards the finalization section 410 after sterilizing the object 306 in the sterilization section 408. At the finalization section 410, the worker or the one or more robots may receive the sterilized object 306. Similarly, multiple objects 306 may be received by the conveyor unit 402 for sterilization and the objects 306 may be sterilized by the sterilization device 102. Thus, the system 400 may enable sterilization of multiple objects 306 in a continuous manner and may be used in multiple industries, as discussed above, for sterilizing multiple objects 306.

The system 400 may further include other units 412. In one example, the other units 412 may include power supply units 414 to supply electrical power to the conveyor unit 402 and the sterilization device 102. The other units 412 may further include control units 416 to control operations of the conveyor unit 402 and the sterilization device 102. For example, the control units 416 may include one or more switches to turn on and turn off the conveyor unit 402 and the sterilization device 102, respectively. The control units 416 may also include one or more buttons that may be used by an operator to modify power being supplied to the sterilization device 102. For example, the operator may define a negative potential voltage supplied to the thermionic cathode 110 by the low voltage supply unit 218, the positive potential voltage that may be supplied to the anode grid 112 by the low voltage supply unit 218, and the positive potential voltage supplied to the anode wire 114 by the high voltage supply unit 220. The control units 416 may also include one or more buttons that may be used by the operator to operate the gas supply unit 204 to supply the ionized gas into the toroidal housing 104 and operate the vacuum pump 214 to withdraw the ionized gas from within the toroidal housing 104.

FIG. 4B illustrates a covering unit 418 that may optionally be placed over the conveyor unit 402 and the sterilization device 102. In one example, the covering unit 418 may secure the conveyor unit 402 and the sterilization device 102 from any external pollutants that may not be desirable for functioning of the conveyor unit 402 and the sterilization device 102. Examples of the external pollutants may include, but may not be limited to, polluted air, dust, moisture, and the like. In one example, the covering unit 418 may act as a shield for the sterilization device 102 that may prevent the electron beams from escaping into the surroundings. Further, the covering unit 418 may be externally fixed with radiation monitoring system (not shown) to measure and display beta particles radiation levels in the surrounding area.

Further, the covering unit 418 may include one or more windows 420. In one example, the one or more windows 420 may be opened to improve air circulation inside the covering unit 418. In another example, the one or more windows 420 may enable the operator to check functioning of the system 400 through the windows, without any requirement to remove the covering unit 418.

Although examples for the present subject matter have been described in language specific to structural features and/or methods, it should be understood that the appended claims are not limited to the specific features or methods described. Rather, the specific features and methods are disclosed and explained as examples of the present subject matter.

I claim:

1. A sterilization device to sterilize an object, the sterilization device comprising:
   a toroidal housing having an outer wall, an inner wall and a central cavity defined by the inner wall, wherein the central cavity is to receive the object to be sterilized, the toroidal housing comprises:
   a thermionic cathode to release one or more primary electrons;
   an anode grid to attract and accelerate the one or more primary electrons to obtain accelerated primary electrons on heating, wherein the thermionic cathode is at least one of a conical shaped cathode electrode and a parabolic shaped cathode electrode, and wherein the thermionic cathode comprises a coating of a work function emitter to increase a number of electrons in the one or more primary electrons emitted from the thermionic cathode; and
   an anode wire to pull one or more additional electrons, wherein the one or more additional electrons are released from a gas plasma discharge within the toroidal housing,
   wherein the anode wire is to accelerate the one or more additional electrons and the accelerated primary electrons to create a spray of accelerated electrons, wherein the spray of accelerated electrons is to be released through the inner wall towards the object to be received by the central cavity, and
   wherein the spray of accelerated electrons is to collide with at least one surface of the object to sterilize the object.

2. The sterilization device as claimed in claim 1, wherein the thermionic cathode, the anode grid, and the anode wire are placed within a hollow space formed between the outer wall and the inner wall of the toroidal housing, and
   wherein the thermionic cathode is placed in close proximity with the outer wall, the anode grid is placed in close proximity to the thermionic cathode, and the anode wire is placed adjacent to the anode grid and in close proximity with the inner wall.

3. The sterilization device as claimed in claim 1, wherein the inner wall comprises a perforated surface to release the spray of accelerated electrons towards the object received in the central cavity, wherein the perforated surface comprises one or more windows to release the spray of accelerated electrons.

4. The sterilization device as claimed in claim 1, wherein the gas plasma discharge comprises one or more ions, wherein the one or more primary electrons collide with the one or more ions to release the one or more additional electrons from the gas plasma discharge, and wherein the one or more additional electrons and the one or more primary electrons further collide with the one or more ions to further release the one or more additional electrons.

5. The sterilization device as claimed in claim 1, wherein the work function emitter is at least one of a Lanthanum hexaboride (LaB6), barium hexaboride (BaB6), Barium oxide (BaO/BaO2) zirconium diboride (ZrB2), hafnium nitride (HfN), and a Cerium hexaboride (CeB6).

6. The sterilization device as claimed in claim 1, further comprises:
   a low voltage supply unit to supply a negative potential voltage to the thermionic cathode to heat the thermionic cathode and a positive potential voltage to the anode grid to attract and accelerate the one or more primary electrons;
   a high voltage supply unit to supply a positive potential voltage to the anode wire to pull the one or more additional electrons and accelerate the one or more additional electrons and the accelerated primary electrons;
   a vacuum pump to create a vacuum inside the toroidal housing;
   a gas supply unit to supply a gas for the gas plasma discharge;
   a flow control valve to receive the gas from the gas supply unit and allow the gas to be injected in the toroidal housing; and
   a pressure measuring unit to measure a pressure of the gas inside the toroidal housing.

\* \* \* \* \*